United States Patent [19]

Aoyama et al.

[11] Patent Number: 5,246,836
[45] Date of Patent: Sep. 21, 1993

[54] PEROXIDASE CATALYZED ENZYME ASSAY BY SAMPLE PRG-TREATMENT

[75] Inventors: Norihito Aoyama, Shizuoka; Mitsuru Tsuda, Mishima; Yoshiaki Shimizu; Seiji Sekine, both of Shizuoka; Toshio Tatano, Numazu, all of Japan

[73] Assignee: Kyowa Medex Co., Ltd., Tokyo, Japan

[21] Appl. No.: 562,592

[22] Filed: Aug. 3, 1990

[30] Foreign Application Priority Data

Aug. 4, 1989 [JP] Japan .................. 1-202677

[51] Int. Cl.$^5$ .................. C12Q 1/60; C12Q 1/58; C12Q 1/28; G01N 33/92
[52] U.S. Cl. .................. 435/11; 435/12; 435/28; 436/13; 436/71
[58] Field of Search .............. 435/11, 12, 28; 436/13, 436/71

[56] References Cited

U.S. PATENT DOCUMENTS

| | | | |
|---|---|---|---|
| 4,416,982 | 11/1983 | Tsuda | 435/11 |
| 4,636,464 | 1/1987 | Nakanishi | 435/14 |
| 4,681,841 | 7/1987 | Matsumoto | 435/18 |
| 4,820,416 | 4/1989 | Chang | 210/632 |
| 4,954,451 | 9/1990 | Albarella | 436/175 |

FOREIGN PATENT DOCUMENTS 0054358 6/1982 European Pat. Off. .
9007115 6/1990 PCT Int'l Appl. .

*Primary Examiner*—Michael G. Wityshyn
*Assistant Examiner*—Ralph Gitomer
*Attorney, Agent, or Firm*—Michael N. Meller

[57] ABSTRACT

A method for determination of an analyte in a sample containing reducing substances is disclosed. After the decomposition of the reducing substances by reaction with hydrogen peroxide formed by enzymatic Redox reaction using a component in the sample which does not participate in another enzymatic Redox reaction using the analyte, the remaining hydrogen peroxide is decomposed, and then the analyte is subjected to enzymatic Redox reaction to form hydrogen peroxide which is then determined by a known method.

8 Claims, No Drawings

PEROXIDASE CATALYZED ENZYME ASSAY BY SAMPLE PRG-TREATMENT

BACKGROUND OF THE INVENTION

The present invention relates to a method for determination of an analyte in a sample by using enzymatic Redox reaction, in which prior to the enzymatic Redox reaction, reducing substances in the sample are oxidized with hydrogen peroxide formed by another enzymatic Redox reaction in the presence of peroxidase.

It is known that a component in a biological sample can be determined by oxidizing the component with oxidase specific for the component in the presence of oxygen to form hydrogen peroxide and determining the formed hydrogen peroxide by a method known per se.

It is also known that when the component cannot be directly oxidized, the component is converted to a compound which can be directly oxidized with oxidase and then the above method is applied to the compound.

The determination of hydrogen peroxide is usually carried out by allowing the hydrogen peroxide to react with a chromogen in the presence of peroxidase to form a pigment and measuring the absorbance of the reaction mixture colored by the formation of the pigment.

The method described above is susceptible to interference from various substances present in the biological sample, for example, reducing substances such as bilirubin, cysteine, glutathione and medicines administered.

Especially, interference from reducing substances such as bilirubin (both conjugated and free types) is serious, which makes it difficult to accurately determine the component.

In order to reduce the influence of such reducing substances, studies have been made on methods in which an enzyme capable of decomposing reducing substances, e.g., bilirubin oxidase, is utilized. However, such methods have the problem that a long period of time is required for the decomposition of the reducing substances.

It is also known that hydrogen peroxide is effective for the decomposition of reducing substances [Bulletin of the Society of Clinical and Hygienic Assayers in Kyoto Prefecture, Japan, Vol. 10, No. 2, p. 31–36 (1983)]. However, when hydrogen peroxide is added directly to a sample, there occurs undesirable decomposition of the component to be determined due to the excessively strong oxidizing power of hydrogen peroxide. In addition to this, the use of hydrogen peroxide is not suitable for the production of an assay composition in the form of a marketable kit.

No method has thus far been found which enables avoidance of the undesirable interference from reducing substances contained in a sample and which is suitable for the production of a marketable assay kit.

As a result of studies on the decomposition of reducing substances in a biological sample, it has been found that the utilization of hydrogen peroxide formed by enzymatic Redox reaction using a component in the sample other than the component to be determined is very effective and does not involve the problems described above.

In this connection, U.S. Pat. No. 4,416,982 discloses a method for determination of an analyte which can be converted by the action of an enzyme (B) to the compound (A) which can be directly oxidized by the action of an oxidase capable of oxidizing the compound (A), which comprises the following steps:

(1) compound (A) in the original sample is oxidized by the action of the oxidase to form hydrogen peroxide;

(2) the resultant hydrogen peroxide is decomposed by adding peroxidase and phenol, aniline or derivatives thereof;

(3) the analyte is converted to compound (A) by the action of enzyme (B);

(4) the resultant compound (A) is oxidized by the action of the oxidase to form hydrogen peroxide; and (5) the resultant hydrogen peroxide is determined by a known method.

The U.S. patent is silent about the decomposition of reducing substances. On the other hand, in the present invention, a component which does not perticipate in enzymatic Redox reaction using the analyte is used for the decomposition of reducing substances as described below.

SUMMARY OF THE INVENTION

In accordance with the present invention, a component in a sample which is to be determined (hereinafter referred to as "analyte") can be determined by: forming hydrogen peroxide in an amount sufficient to decompose reducing substances in the sample by enzymatic Redox reaction (1) using a component (Y) in the sample which does not participate in enzymatic Redox reaction (2) using the analyte; oxidizing the reducing substances with the formed hydrogen peroxide in the presence of peroxidase; inactivating the enzyme used in the enzymatic Redox reaction (1), if necessary; decomposing the remaining hydrogen peroxide with peroxidase and a compound (X) capable of being converted into a radical by the reaction with hydrogen peroxide in the presence of peroxidase; forming hydrogen peroxide by the enzymatic Redox reaction (2) using the analyte; and determining the formed hydrogen peroxide by a method known per se.

DETAILED DESCRIPTION OF THE INVENTION

When the analyte is a substrate which cannot be directly oxidized with an oxidase, the analyte is converted with an appropriate enzyme into a substrate which can be directly oxidized.

When the analyte is an enzyme, the substrate for the enzyme is added to the sample, if necessary, together with appropriate substrate and enzyme to form a substrate which can be directly oxidized.

Examples of the analyte which can be directly oxidized include free form of cholesterol, glycerol, glucose, choline, pyruvic acid (pyruvate), uric acid (urea), sarcosine, and lactic acid (lactate).

Examples of the analyte which is converted into a substrate which can be directly oxidized include ester form of cholesterol, triglyceride, phospholipid, L-alanine, L-aspartic acid, oxaloacetic acid, starch, maltose, sialic acid, creatine and creatinine.

Reactions for the determination of the analytes which are converted into substrates which can be directly oxidized are illustrated below.

(1) Cholesterol ester

Cholesterol ester

↓ Cholesterol esterase

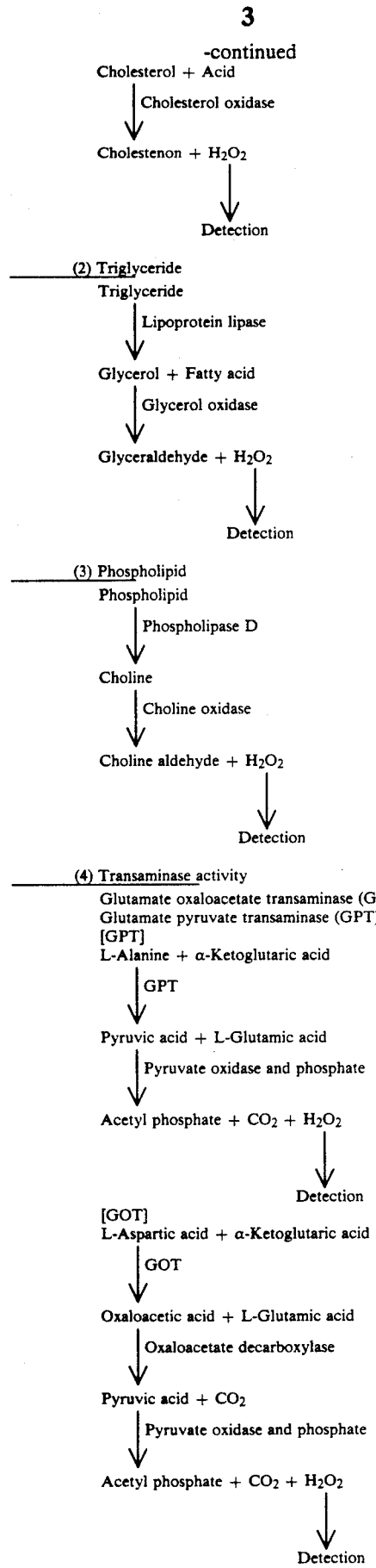

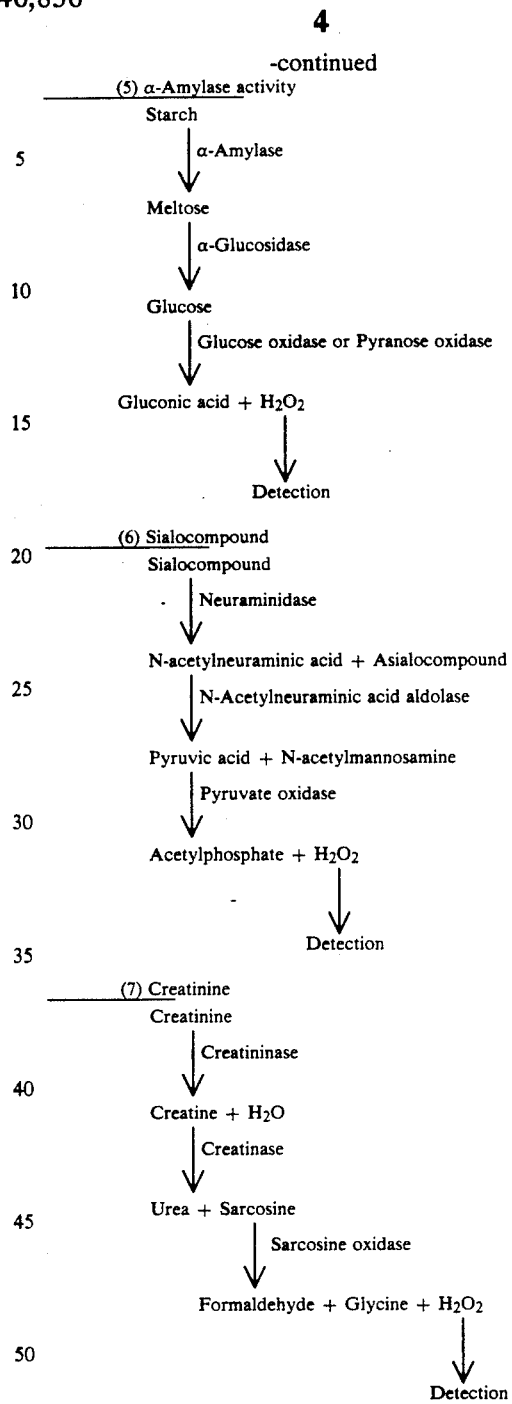

An example of the analyte which is enzyme is choline esterase.

As the component (Y) for the enzymatic Redox reaction (1), any component may be used so long as hydrogen peroxide is formed by the reaction and it does not participate in the enzymatic Redox reaction (2) using the analyte.

The component which participates in the enzymatic Redox reaction (2) using the analyte means the following: when the analyte is a substrate which can be directly oxidized, it means the analyte itself; when the analyte is converted into a substrate which can be directly oxidized, it means the analyte itself and the substrate and enzyme used in the enzymatic conversion; and when the analyte is an enzyme, it means the analyte itself and the substrate and enzyme necessary for the formation of hydrogen peroxide from the analyte.

Examples of the component (Y) include the same substances as those mentioned as examples of the analyte.

Usually, a component which can be directly oxidized is used as the component (Y).

The number of the component (Y) is not limited to one, and two or more such components may be used.

If the sample to be assayed contains no component (Y) or contains the component (Y) in an amount insufficient to oxidize reducing substances in the sample, an appropriate substrate and oxidase for the substrate may be added to the sample for effecting the enzymatic Redox reaction (1).

As the compound (X), any compound may be used so long as it reacts with hydrogen peroxide in the presence of peroxidase to form a radical which is a non-coloring compound.

Examples of the compound (X) include the compounds represented by Formula (I):

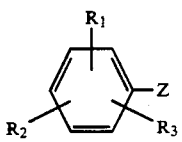

wherein Z is OH or $NR_4R_5$ wherein $R_4$ and $R_5$ are the same or different and represent hydrogen atom, alkyl, substituted alkyl or acyl, and $R_1$, $R_2$ and $R_3$ are the same or different and represent hydrogen atom, halogen atom, alkyl, alkoxy, amino, nitro, carboxyl or sulfonyl.

In the above definition, alkyl means alkyl having 1–5 carbon atoms such as methyl, ethyl, propyl, butyl and pentyl. Substituents of substituted alkyl include hydroxyl, amino and acylamino and acyl in acylamino has the same significance as that in $R_4$. Acyl means acyl having 1–5 carbon atoms such as formyl, acetyl, propionyl and butyryl. Alkoxy means alkoxy having 1–5 carbon atoms such as methoxy, ethoxy, propoxy and butoxy.

Specific examples of the compound (X) include phenol, 2,4-dichlorophenol, p-chlorophenol, 2,4-dibromophenol, p-bromophenol, 2,3-dichlorophenol, 2-nitrophenol, 3-nitrophenol, 2-aminophenol, 3-aminophenol, aniline, 2-bromoaniline, 3-bromoaniline, 2-chloroaniline, 3-chloroaniline, o-toluidine, m-toluidine, dimethylaniline, diethylaniline, o-phenylenediamine, N,N-p-phenylenediamine, o-anisidine, m-anisidine, o-cresol, m-cresol, 2-methyl-2,6-dinitrophenol, 2-methoxy-5'-nitroaniline, 2-methyl-5-nitroaniline, 3,5-dihydroxytoluene, 3-methoxyphenol, 2-amino-5-methylphenol, 2-hydroxy-3-methylbenzoic acid, 2-hydroxyphenylacetic acid, 2,3-dimethylphenol, 2,5-dimethylphenyl, 2-ethylphenol, 3-ethylphenol, 2-methoxymethylphenol, 2,3-dimethylaniline, 2,5-dimethylaniline, 3,5-diethylaniline, 3-(dimethylamino)phenol, 3-methoxy-N,N-dimethylaniline, N,N-diethyl-1,3-phenylenediamine, 3,5-dimethyl-1,2-phenylenediamine and 4-aminoantipyrine.

The determination of the analyte may be achieved by carrying out reactions stepwise, or conveniently by appropriately combining the following steps A and B.

Step A: (Decomposition of Reducing Substances)

I. In cases where the component (Y) is a component in a sample which can be directly oxidized, the sample, the oxidase for the component, peroxidase and compound (X) are added to an appropriate buffer solution.

In this step, the component (Y) is oxidized with the oxidase in the presence of oxygen to form hydrogen peroxide. Then, reducing substances in the sample are oxidized with the formed hydrogen peroxide in the presence of peroxidase and the compound (X). The remaining hydrogen peroxide reacts with the compound (X) to form a radical. As the oxidation reaction of the reducing substances proceeds faster than the formation of the radical, the reducing substances are completely oxidized in a short period of time, even if the reaction of hydrogen peroxide with the compound (X) simultaneously proceeds.

Though the oxidation reaction of the reducing substances can proceed without the compound (X), it is accelerated by the use of the compound (X).

II. In cases where the component (Y) is substrate (A) which cannot be directly oxidized, the sample, an enzyme necessary for the conversion of the substrate (A) into substrate (B) which can be directly oxidized, the oxidase for the substrate (B), peroxidase and compound (X) are added to an appropriate buffer solution.

In this step, the substrate (A) is converted into the substrate (B) first and then the same reactions as described in Step A-I occur. If any other substrate, compound or enzyme is required in the conversion reaction, such substances are also added to the buffer solution.

III. In cases where the component (Y) is an enzyme, the sample, substrate (A) for the enzyme, the oxidase for the substrate (B) which is obtained by conversion of the substrate (A), peroxidase and compound (X) are added to an appropriate buffer solution.

After completion of the oxidation of reducing substances, an inactivating agent for the enzyme used as the component (Y) is added to the reaction mixture.

In this step, the formation of the substrate (B) is effected first and then the same reactions as described in Step A-I occur. If any other substrate and enzyme are required in the conversion reaction, they are also added to the buffer solution.

Step B: (Determination of analyte)

As the method for the determination of hydrogen peroxide, any method known per se may be used and one of the most popular methods is described.

That is, the hydrogen peroxide formed in the enzymatic Redox reaction (2) is allowed to react with a chromogen in the presence of peroxidase to form a pigment and the absorbance of the reaction mixture colored by the formation of the pigment is measured.

I. In cases where the analyte is a substrate which can be directly oxidized, the oxidase for the analyte and a chromogen are added to the reaction mixture obtained in Step A to effect the oxidation reaction.

The absorbance of the reaction mixture is measured at $\lambda_{max}$ of the chromogen utilized.

In this step, a pigment is formed by the oxidation reaction, whereby color is developed.

II. In cases where the analyte is a component which cannot be directly oxidized, an enzyme and/or a substrate necessary for forming hydrogen peroxide stoichiometrically using the component, and a chromogen are added to the reaction mixture obtained in Step A.

The absorbance of the reaction mixture is measured at $\lambda_{max}$ of the chromogen utilized.

In this step, when the component is a substrate, it is converted to another substrate which can be directly oxidized.

When the component is an enzyme, the substrate for the enzyme is added to the reaction mixture of Step A to obtain another substrate which can be directly oxidized.

In both cases, a pigment is formed by oxidation reaction, whereby color is developed.

As the chromogen used in the present invention, chromogen may be used so long as it reacts with hydrogen peroxide in the presence of peroxidase to form stoichiometrically a pigment.

Compound (X) may be used as a part of chromogen. In this case, a coupler such as 4-aminoantipyrine (hereinafter referred to as "4-AA"), 3-methyl-2-thiazolinone hydrazone (hereinafter referred to as MBTH), or 4,4',4''-methylidynetris may be used in combination with the compound (X).

The compound represented by the following formula may be used as a chromogen.

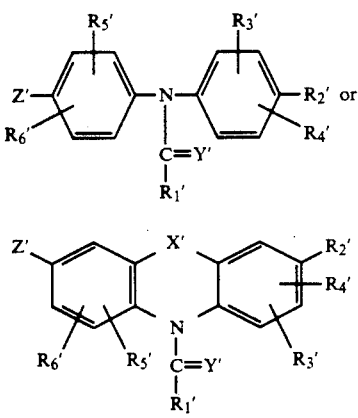

In the formula, Z' represents hydroxyl amino or substituted amino, Y' represents oxygen atom or sulfur atom, $R'_1$ represents hydrogen, alkyl, alkenyl, aryl, amino or monosubstituted amino, $R'_2$ represents hydrogen, hydroxyl, alkyl, alkenyl, aryl, amino, alkyl-amino or alkoxy, $R'_3$, $R'_4$, $R'_5$ and $R'_6$ represent hydrogen, alkyl, alkenyl, acyl, aryl, halogen, sulfo, nitro, carboxyl, hydroxyl, hydroxyalkyl or alkoxy, $R'_3$ and $R'_4$ or $R'_5$ and $R'_6$ may form alkenylene, X' represents —S—, —O—,

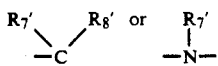

$R'_7$ and $R'_8$ represent hydrogen, alkyl, alkenyl or aryl (U.S. Pat. No. 4,384,042).

Further, the chromogen described in U.S. Pat. No. 4,810,642 may be used.

When the analyte in a sample is substrate (A) which cannot be directly oxidized, the substrate (A) is converted to substrate (B), which is then oxidized with the oxidase for the substrate (B) to form hydrogen peroxide, followed by determination of the hydrogen peroxide.

In the method described above, if the sample contains both the substrate (A) and the substrate (B), the substrate (B) originally contained in the sample must be removed or decomposed prior to the determination of the substrate (A).

In such a case, the oxidase for the substrate (B) is added to a buffer solution in Step A to oxidize the substrate (B) originally contained in the sample and the hydrogen peroxide formed by oxidation reacts with reducing substances in the sample or reacts with compound (X) to form a radical.

For example, determination of ester form of cholesterol in a sample containing free form of cholesterol and ester form of cholesterol can be carried out in the following manner. That is, cholesterol oxidase is added to the sample to oxidize the free form of cholesterol and the hydrogen peroxide formed by oxidation is allowed to react with a coupler such as phenol and 4-aminoantipyrine, whereby the hydrogen peroxide is decomposed.

Then, the ester form of cholesterol is determined by converting to free form of cholesterol by esterase; oxidizing the free form of cholesterol with cholesterol oxidase to form hydrogen peroxide; allowing the hydrogen peroxide to react with phenol and 4-aminoantipyrine in the presence of peroxidase to form a pigment; and measuring the absorbance of the reaction mixture colored by the formation of the pigment.

In this case, cholesterol oxidase is added to a buffer solution in Step A, whereby the free form of cholesterol in the original sample is oxidized with cholesterol oxidase to form hydrogen peroxide, which is then utilized in the oxidation of the reducing substances or decomposed by the reaction with the compound (X). Thus, Step B can be carried out by one step, that is, the addition of cholesterol esterase and a chromogen to the reaction mixture obtained in Step A.

In carrying out the determination, the enzymatic reaction is usually carried out at a temperature of 5°–50° C., preferably 25°–40° C. in a buffer solution having a pH of 2–10 and is completed in several minutes.

The chromogen is used in an equimolar amount with hydrogen peroxide or more, preferably 10–1000 mole equivalents. Enzymes are used in a concentration of 0.1–1000 IU/ml, preferably 1–100 IU/ml.

As buffers, phosphate buffer, tris-HCl buffer, succinate buffer, citrate buffer, acetate buffer, etc. may be used in a concentration of 0.001–2 mol/l.

The present invention also provides a kit which comprises composition (A) comprising
  (1) oxidase for the component (Y) or a substrate and/or an enzyme necessary for formation of hydrogen peroxide using the component (Y)
  (2) peroxidase and
  (3) compound (X)
and composition (B) comprising
  (1) oxidase for the analyte or a substrate and/or an enzyme necessary for formation of hydrogen peroxide using the analyte and
  (2) chromogen.

Certain embodiments of the present invention are illustrated by the following representative examples.

In the examples, serums substantially containing no reducing substances were used.

EXAMPLE 1

Determination of Creatine

A solution was prepared by dissolving 20 μmol phenol, 10 units of peroxidase and 30 units of sarcosine oxidase in 2.25 ml of 10 mM phosphate buffer (pH 7.4). The same solution was separately prepared, and 4 units of L-lactate oxidase (LOD) was added thereto. To each of the solutions was added 0.06 ml of a 1:1 mixture (based on volume; the same shall apply hereinafter) of a 5 mg/dl creatine solution and purified water, a 1:1 mixture of serum and purified water, a 1:1 mixture of serum and a bilirubin solution having a concentration shown in Table 1, or purified water. The resulting mixtures were subjected to preliminary heating in a thermostat at 37° C. for about 3 minutes to decompose bilirubin.

To each of the mixtures was added a reagent prepared by dissolving 1 μmol 4,4-bis(dimethylamino)diphenyl(2,7-dihydroxy-1-naphthyl)methane and 100 units of creatinase in 0.75 ml of 50 mM N,N-bis(2-hydroxyethyl)-glycine buffer (pH 8.0). After the resulting mixtures were maintained in a thermostat at 37° C. for 10 minutes, the absorbance was measured at a wavelength of 633 nm with a spectrophotometer (Model 228, manufactured by Hitachi, Ltd.) using purified water as a control. The results obtained are shown in Table 1.

TABLE 1

| Sample | Creatine (mg/dl) | |
|---|---|---|
| | without LOD | with LOD |
| Serum + purified water | 2.50 | 2.50 |
| Serum + bilirubin (20 mg/dl) | 1.60 | 2.48 |
| Serum + bilirubin (40 mg/dl) | 1.46 | 2.51 |
| Serum + bilirubin (80 mg/dl) | 0.83 | 2.49 |

EXAMPLE 2

The same procedure as in Example 1 was repeated, except glutathione was used in place of bilirubin. The results obtained are shown in Table 2.

TABLE 2

| Sample | Creatine (mg/dl) | |
|---|---|---|
| | without LOD | with LOD |
| Serum + purified water | 2.50 | 2.50 |
| Serum + glutathione (20 mg/dl) | 1.60 | 2.48 |
| Serum + glutathione (40 mg/dl) | 1.46 | 2.51 |
| Serum + glutathione (80 mg/dl) | 0.83 | 2.49 |

EXAMPLE 3

Determination of Uric Acid

A solution was prepared by dissolving 2.7 μmol N-ethyl-N-(3-methylphenyl)-N'-succinylethylenediamine and 10 units of peroxidase in 1.5 ml of 25 mM potassium hydrogenphthalate buffer (pH 6.5). The same solution was separately prepared, and 10 units of cholesterol oxidase (CHOD) and 5 units of cholesterol esterase (CHER) were added thereto.

To each of the solutions was added 0.08 ml of a 1:1 mixture of a 5 mg/dl uric acid solution and purified water, a 1:1 mixture of serum and purified water, a 1:1 mixture of serum and a bilirubin solution having a concentration shown in Table 3, or purified water. The resulting mixtures were subjected to preliminary heating in a thermostat at 37° C. for 5 minutes to decompose bilirubin.

To each of the mixtures was added a reagent prepared by dissolving 1 μmol 4-aminoantipyrine and 2 units of uricase in 1.5 ml of 0.1M phosphate buffer (pH 6.5). After the resulting mixtures were maintained in a thermostat at 37° C. for about 5 minutes, the absorbance was measured at a wavelength of 555 nm with a spectrophotometer (Model 228, manufactured by Hitachi, Ltd.) using purified water as a control. The results obtained are shown in Table 3.

TABLE 3

| Sample | Uric acid (mg/dl) | |
|---|---|---|
| | without CHER & CHOD | with CHER & CHOD |
| Serum + purified water | 4.2 | 4.2 |
| Serum + bilirubin (20 mg/dl) | 4.0 | 4.2 |
| Serum + bilirubin (40 mg/dl) | 3.8 | 4.2 |
| Serum + bilirubin (80 mg/dl) | 3.5 | 4.1 |

EXAMPLE 4

The same procedure as in Example 3 was repeated, except glutathione was used in place of bilirubin. The results obtained are as shown in Table 4.

TABLE 4

| Sample | Uric acid (mg/dl) | |
|---|---|---|
| | without CHER & CHOD | with CHER & CHOD |
| Serum + Purified water | 4.2 | 4.2 |
| Serum + glutathione (20 mg/dl) | 4.1 | 4.2 |
| Serum + glutathione (40 mg/dl) | 3.9 | 4.2 |
| Serum + glutathione (80 mg/dl) | 3.8 | 4.2 |

EXAMPLE 5

Determination of Lactic Acid

A solution was prepared by dissolving 3.6 μmol 4-aminoantipyrine, 38 units of peroxidase and 7 units of choline oxidase in 2.5 lm of 60 mM Tris buffer (pH 7.5). The same solution was separately prepared, and 1.5 μmol o-toluoylcholine (OTCCP: a substrate for choline esterase) was added thereto. To each of the solutions was added 0.04 ml of a 1:1 mixture of a 40 mg/dl L-lactic acid solution and purified water, a 1:1 mixture of serum and purified water, a 1:1 mixture of serum and a bilirubin solution having a concentration shown in Table 5, or purified water. The resulting mixtures were subjected to preliminary heating in a thermostat at 37° C. for 5 minutes to decompose bilirubin.

To each of the mixtures was added a reagent prepared by dissolving 1.5 μmol phenol, 0.1 mmol neostigmine (choline esterase inhibitor) and 4 units of L-lactate oxidase in 0.5 ml of 60 mM Tris buffer (pH 7.5). After the resulting mixtures were maintained in a thermostat at 37° C. for about 5 minutes, the absorbance was measured at a wavelength of 500 nm with a spectrophotometer (Model 228, manufactured by Hitachi, Ltd.) using purified water as a control. The results obtained are shown in Table 5.

TABLE 5

| Sample | Lactic Acid (mg/dl) | |
|---|---|---|
| | without OTCC | with OTCC |
| Serum + purified water | 14.9 | 14.9 |
| Serum + bilirubin (20 mg/dl) | 14.2 | 14.9 |
| Serum + bilirubin (40 mg/dl) | 13.7 | 14.8 |
| Serum + bilirubin (80 mg/dl) | 12.4 | 14.9 |

EXAMPLE 6

The same procedure as in Example 5 was repeated, except glutathione was used in place of bilirubin. The results obtained are shown in Table 6.

TABLE 6

| Sample | Lactic Acid (mg/dl) | |
| --- | --- | --- |
| | without OTCC | with OTCC |
| Serum + purified water | 14.9 | 14.9 |
| Serum + glutathione (20 mg/dl) | 14.5 | 15.0 |
| Serum + glutathione (40 mg/dl) | 14.2 | 14.9 |
| Serum + glutathione (80 mg/dl) | 13.6 | 14.8 |

We claim:

1. In a method for determining an analyte in a biological sample by allowing the analyte to react with oxidase for the analyte to form hydrogen peroxide, allowing the hydrogen peroxide to react, in the presence of peroxidase, with a chromogen thus stoichiometrically forming a pigment, and measuring the change of absorbance of the reaction mixture colored by the formation of the pigment, the improvement comprising:

pretreating the biological sample prior to the determination by forming hydrogen peroxide in an amount sufficient to decompose reducing substances in the sample by enzymatic reaction of a substrate other than the analyte assayed;

oxidizing the reducing substances with the formed hydrogen peroxide in the presence of peroxidase; and decomposing the remaining hydrogen peroxide with peroxidase and a compound capable of being oxidized to a non-coloring radical by reaction with hydrogen peroxide in the presence of peroxidase.

2. The method according to claim 1, wherein said analyte is a member selected from the group consisting of urea, free form of cholesterol, choline, glucose, lactate, glycerol and pyruvate.

3. The method according to claim 1, wherein said analyte is a substrate resulting from another substrate in the biological sample by enzymatic reaction.

4. The method according to claim 1, wherein oxidation of the reducing substances is carried out in the presence of a compound capable of being oxidized to a non-coloring radical by reaction with hydrogen peroxide in the presence of peroxidase.

5. The method according to claim 1, wherein a second, distinct substrate other than the analyte to be assayed is originally present in the sample.

6. The method according to claim 1 wherein said substrate is a member selected from the group consisting of creatine, urea, lactate, free form of cholesterol, ester form of cholesterol, glucose, pyruvate and phospholipid.

7. The method according to claim 1, wherein said compound is selected from the group consisting of phenol, 2,4-dichlorophenol, p-chlorophenol, 2,4-dibromophenol, p-bromophenol, 2,3-dichlorophenol, 2-nitrophenol, 3-nitrophenol, 2-aminophenol, 3-aminophenol, aniline, 2-bromoaniline, 3-bromoaniline, 2-chloroaniline, 3-chloroaniline, o-toluidine, m-toluidine, dimethylaniline, diethylaniline, o-phenylenediamine, N,N-p-phenylenediamine, o-anisidine, m-anisidine, lo-cresol, m-cresol, 2-methyl-2,6-dinitrophenol, 2-methoxy-5-nitroaniline, 2-methyl-5-nitroaniline, 3,5-dihydroxytoluene, 3-methoxyphenol, 2-amino-5-methylphenol, 2-hydroxy-3-methylbenzoic acid, 2-hydroxyphenylacetic acid, 2,3-dimethylphenol, 2,5-dimethylphenol, 2-ethylphenol, 3-ethylphenol, 2-methoxymethylphenol, 2,3-dimethylaniline, 2,5-dimethylaniline, 3,5-diethylaniline, 3-(dimethylamino)-phenol, 3-methoxy-N,N-dimethylaniline, N,N-diethyl-1,3-phenylenediamine, 3,5-dimethyl-1,2-phenylenediamine, N-ethyl-N-(3-methylphenyl)-N'-acetylethylenediamine and 4-aminoantipyrine.

8. A method for the determination of creatine in a biological sample which comprises: adding, to the sample, lactate oxidase, sarcosine oxidase, peroxidase and a compound capable of being oxidized to a non-coloring radical by the reaction with hydrogen peroxide in the presence of peroxidase to effect formation of hydrogen peroxide, oxidizing reducing substances and then decomposing the remaining hydrogen peroxide; adding creatinase and a chromogen to the resultant mixture to effect formation of hydrogen peroxide and then formation of a pigment; and measuring the absorbency of the reaction solution colored by the formation of the pigment.

* * * * *